United States Patent
Altink et al.

(10) Patent No.: US 10,221,124 B2
(45) Date of Patent: Mar. 5, 2019

(54) PROCESS FOR THE PREPARATION OF DIAMINOBUTANE

(71) Applicant: DSM IP Assets B.V., Heerlen (NL)

(72) Inventors: Rinke Marcel Altink, Echt (NL); Anna Maria Cornelia Francisca Castelijns, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/557,322

(22) PCT Filed: Mar. 15, 2016

(86) PCT No.: PCT/EP2016/055541
§ 371 (c)(1),
(2) Date: Sep. 11, 2017

(87) PCT Pub. No.: WO2016/146627
PCT Pub. Date: Sep. 22, 2016

(65) Prior Publication Data
US 2018/0050981 A1 Feb. 22, 2018

(30) Foreign Application Priority Data
Mar. 17, 2015 (EP) .................................... 15159487

(51) Int. Cl.
*C07C 209/78* (2006.01)
*C07C 209/68* (2006.01)

(52) U.S. Cl.
CPC .......... *C07C 209/78* (2013.01); *C07C 209/68* (2013.01)

(58) Field of Classification Search
None
See application file for complete search history.

(56) References Cited

FOREIGN PATENT DOCUMENTS

| EP | 1 527 776 | 5/2005 |
|---|---|---|
| JP | 2014-169230 | 9/2014 |

OTHER PUBLICATIONS

International Search Report and Written Opinion of the ISA for PCT/EP2016/055541, dated May 17, 2016, 6 pages.
Richards et al., "The stereochemistry of the enzymic decarboxylation of L-arginine and of L-ornithine", Canadian Journal of Chemistry, vol. 60, No. 22, Jan. 1, 1982.
Hashimoto et al., "A Novel Decarboxylation of Alpha-Amino Acids. A Facile Method of Decarboxylation by the Use of 2-Cyclohexen-1-One As a Catalys", Chemistry Letters, Jan. 1986, pp. 893-896.

*Primary Examiner* — Clinton A Brooks
(74) *Attorney, Agent, or Firm* — Nixon & Vanderhye P.C.

(57) ABSTRACT

The present invention relates to a process for the preparation of diaminobutane from ornithine, comprising steps of: i. preparing a solution of (a) a salt of ornithine and an acid; and (b) an aldehyde or a ketone, or a mixture thereof; in (c) a solvent, wherein the solvent comprises a protic organic solvent or a dipolar aprotic organic solvent, or a mixture thereof and ii. heating the solution to a temperature above 100° C., thereby inducing decarboxylation of the ornithine and formation of diaminobutane.

24 Claims, No Drawings

PROCESS FOR THE PREPARATION OF DIAMINOBUTANE

This application is the U.S. national phase of International Application No. PCT/EP2016/055541 filed 15 Mar. 2016, which designated the U.S. and claims priority to EP Patent Application No. 15159487.6 filed 17 Mar. 2015, the entire contents of each of which are hereby incorporated by reference.

The invention relates to a process for the preparation of diaminobutane from ornithine.

Decarboxylation of α-amino-acids is a known method to produce amino compounds. For example, diaminobutane can be prepared by enzymatic decarboxylation from ornithine. Typically, enzymes suitable for such a process are expensive, the process is performed in highly diluted aqueous solutions, and isolation of the diaminobutane form the fermentation broth is laborious and costly. Alternatively, the enzyme is first isolated form the host. Such a process is described, for example, by J. C. Richards et. al, in "The stereochemistry of the enzymatic decarboxylation of L-arganine and of L-ornithine", Can. J. Chem., 60 (22), 2810-2820. This article describes a process for preparing diaminobutane by decarboxylation of ornithine in aqueous medium catalyzed by L-ornithine decarboxylase (EC 4.1.1.17) of *E. coli*. The process is done in aqueous medium, while for the isolation organic solvents are used.

Several procedures for the decarboxylation of α-amino acids are described in the literature such as thermal decarboxylation, decarboxylation with peroxides as a catalyst or decarboxylation in the presence of ketones or aldehydes. The decarboxylation of L- or D,L-tryptophan into tryptamine can be accomplished by heating tryptophan in diphenylmethane as a solvent (T. Kametani et al. In Synthesis (1972), 475 and further). After refluxing of tryptophan in diphenylmethane as a solvent (boiling temperature 264° C.) for 5-20 min., followed by treatment with dry HCl, the crude tryptamine. HCl salt could be obtained in 93% yield. After re-crystallization from ethanol/ethyl acetate the pure tryptamine hydrochloride (melting point 248-249° C.) could be obtained as colorless crystals in 63% yield. Decarboxylation of α-amino acids is also possible by distillation under an Argon atmosphere (EP 1527776). In this way (R)-3-hydroxy-pyrrolidine was obtained in a yield of 72% by thermal decarboxylation of (2S,3R)-3-hydroxypyrrolidine-2-carboxylic acid. The thermal decarboxylation of α-amino acids in an inert medium is accelerated in the presence of organic peroxides as catalysts (G. Chatelus, Bulletin de la Societé Chimique de France (1964), 10, 2523-32; S. Kanao, in Yakugaku Zasshi (1947), 67, 243-244; and Ajinomoto Co in Yakugaku Zasshi (1964), 84, 1014-16). For example, 1-leucine is decarboxylated into isopentylamine by heating in tetralin in the presence of tetralin peroxide as a catalyst. Depending on the purity of the tetralin used, isopentylamine might be obtained in 80-95% yield. Heating of α-amino acids with one or more equivalents of a ketone or aldehyde, produces the amines corresponding to the amino acids.

A. F. Al-Sayyab et al. (J. Chem. Soc. (C) (1968), 406-410) describe the decarboxylation/transamination of α-amino acids in the presence of equimolar amounts of (ring substituted) acetophenones or benzophenones. However, apart from decarboxylation, transamination might occur, resulting in the formation of ketones.

G. Chatelus (Bulletin de la Societé Chimique de France (1965), 4, 929-933) describes the decarboxylation of α-amino acids by reaction with an excess of a ketone or aldehyde. For instance, reaction of leucine with an excess (5.56 mol equiv.) of diamyl ketone at 155° C., followed by acidic hydrolysis results in the formation of the HCl salt of isopentylamine. The disadvantage of the use of one or more equivalents of a ketone or aldehyde is the formation of the Schiff's base of the amine, which has to be hydrolysed under acidic conditions resulting in an aqueous solution of the salt of the amine, from which the amine, after neutralization has to be isolated (e.g. by extraction).

Also S. Wallbaum et al in Synthetic Communications, 24(10), 1381-1387 (1994), describe the decarboxylation of α-amino acids by reaction with an excess of a ketone or aldehyde in a high boiling solvent. The α-amino acids are for example L-theonine (2S,3R)-1, L-hydroxyproline (2S, 4R)-2 and the bicyclic proline analogue (1R,3R,5R)-5. The catalyst used is 2-cyclohexen-1-one and as solvent a glycol ether, more particular tetraethylene glycol dimethylether is used, and the decarboxylation is carried out at 170° C.

Patent application JP 2014 169230 A describes a method for preparing an alkylene polyamine from an amino acid having an aminoalkyl group, e.g. lysine or ornithine by decarboxylation reaction at 160-300° C. in the presence of a cyclic ketone which is the liquid state at 160-300° C. In all examples herein lysine was used.

The procedures in which the decarboxylation is executed thermally in a high boiling solvent optionally in the presence of catalytic amounts of a ketone or aldehyde (as described by S. Takano et al, Heterocycles (1977), 6 (8), 1167-1171; K. Rossen et al, Synthetic Communications (1993), 23 (8), 1071-74; H. Mitsunori, et al, Chemistry Letters (1986), 893-896; S. Wallbaum et al, Synthetic Communications (1994), 24 (10), 1381-7; ref. 8-11) and Patent application JP 2014 169230 A is therefore more attractive for production on commercial scale, since the amine is obtained directly in an organic solvent from which it can be isolated e.g. by distillation. For instance, reaction of lysine with a catalytic amount of 2-cyclohexene-1-one in cyclohexanol (boiling point 160-161° C.) as a solvent, results in the formation of 1,5-diaminopentane in high yields, which might be recovered/purified by distillation. It was therefore expected that if similar reactions were executed with ornithine as a starting material this would result in the formation of 1,4-diaminobutane.

The inventors have tested several options, but found that either no reaction occurred or that serious side reactions occurred resulting in ring-closed products instead of the desired 1,4-diaminobutane.

The aim of the invention has therefore been to provide a process for the preparation of diaminobutane from ornithine, that is effective and results in good yields without many side products.

This aim has been achieved with the process according to the invention, comprising the following steps:
 i. preparing a solution of
   (a) a salt of ornithine and an acid; and
   (b) an aldehyde or a ketone, or a mixture thereof; in
   (c) a solvent, wherein the solvent comprises a protic organic solvent or a dipolar aprotic organic solvent, or a mixture thereof, and
 ii. heating the solution to a temperature above 100° C. thereby inducing decarboxylation of the ornithine and formation of diaminobutane.

The effect of the process according to the invention, comprising the use of a salt of ornithine in combination with an aldehyde or a ketone, or a mixture thereof, in a protic organic solvent or a dipolar aprotic organic solvent, or in a mixture thereof, is that nearly quantitative decarboxylation of ornithine is achieved in relatively short time and that hardly any to no ring formation is obtained. This is in contrast with the process starting from ornithine rather than from a salt of ornithine or executed in an apolar solvent. The process executed in cyclohexanol with a catalytic amount of 2-cyclohexene-1-one while starting from ornithine produces predominantly ring closure rather than decarboxylation of ornithine. In contrast herewith, with the corresponding process performed in an apolar solvent, such as diethyleneglycol dimethyl ether, also known as diglyme, no reaction occurred.

Solvents may be characterized in three broad categories; protic solvents, polar aprotic solvents, and apolar solvents.

Protic solvents are typically polar. Protic solvents, such as for example water, alcohols, and carboxylic acids, have high polarity and are hydrogen bond donors. Polar aprotic solvents, such as for example ketones, sulfones, sulfoxides, and nitriles, cannot donate labile hydrogen atoms to form strong hydrogen bonds, but have a medium polarity due to a sizable permanent dipole moment. Polar aprotic solvents are therefore also known as dipolar aprotic solvents. Generally, such (di)polar aprotic solvents can form hydrogen bonds with solvents capable of donating labile hydrogen atoms. Apolar aprotic solvents, such as for example aliphatic, cycloaliphatic, and aromatic hydrocarbons, have very low to negligible polarity, are not hydrogen bond donors, and generally do not form hydrogen bonds with solvents capable of donating labile hydrogen atoms. These solvents are typically not miscible with water. Examples thereof are diglyme, hexane, benzene, diethyl ether.

Within the context of the present invention, a solvent is understood to be a substance capable of dissolving another substance therein. Typically, the substance used as a solvent is a liquid at the temperature at which the other substance has to be dissolved. Suitably, the substance used as the solvent is a liquid at room temperature and atmospheric pressure (i.e. about 0.1 MPa).

An organic solvent is herein understood to be a liquid substance with a chemical structure comprising at least one carbon atom in the chemical structure.

Within the context of the present invention a protic organic solvent is understood to be an organic solvent that has a hydrogen atom bound to an oxygen atom, as in a hydroxyl group, or to a nitrogen atom, as in an amino group.

Within the context of the present invention a dipolar aprotic organic solvent is understood to be an organic solvent not containing a hydrogen atom bound to an oxygen or a nitrogen atom, which solvent possesses a dielectric constant sufficiently high to induce a reaction of the ornithine salt in the solution comprising the ornithine salt, the aldehyde and/or ketone, and the organic solvent.

Suitably, the dipolar aprotic organic solvent has a dielectric constant of at least 10, preferably at least 15. The dielectric constant is herein understood to be the relative permittivity determined by the method according to ASTM D924-08, and measured at 20° C. and 55 Hz. Herein the relative permittivity is calculated from the measured actual permittivity for the substance divided by the actual permittivity for vacuum.

In the process according to the invention, the protic organic solvent or dipolar aprotic organic solvent used preferably has a boiling point of at least 100° C. More preferably the solvent has a boiling point of at least 125° C., still more preferably at least 140° C., or even at least 150° C., and even better of at least 175° C. Herein the boiling point referred to is measured at 0.1 MPa (atmospheric pressure).

Protic organic solvents and dipolar aprotic organic solvents with a boiling temperature at atmospheric pressure below the desired reaction temperature may be applied in combination with a reaction temperature above said boiling point by using a pressure reactor, to allow the reaction to occur at a higher pressure and thereby raising the temperature at which the solvent starts to boil. For example, solvents with a boiling temperature below 140° C. may be applied in combination with a reaction temperature above 140° C. using such a pressure reactor. Also an elevated temperature higher than 250° C. may be applied. Also here, since most solvents have a lower boiling temperature, it will be necessary in many cases to use a pressure reactor. A pressure reactor may also be used in combination with solvents that have a boiling temperature in the range of 140-250° C. to raise the temperature at which the solvent starts to boil and thereby to allow a higher elevated temperature for speeding up the reaction.

With a solvent like DMSO, or benzyl alcohol, both having a high boiling point, it is possible to get short reaction times to complete the decarboxylation without the necessity to use a pressure reactor.

Suitable dipolar aprotic organic solvents are, for example, dimethylformamide (DMF), dimethylsulfoxide (DMSO), acetonitrile, or dimethyl acetamide. Suitable protic organic solvents are alcohols, for example, C1-C12 alcohols such as, methanol, ethanol, propanol, butanol, pentanol, hexanol, heptanol, octanol, decanol, and diols and triols. Examples thereof include 1-propanol, 2-propanol, 1-butanol, 2-butanol, tert. butanol, 1-pentanol, 2-pentanol, 3-pentanol, 1-hexanol, 2-hexanol, 3-hexanol, cyclohexanol, 1-heptanol, 1-octanol, 2-octanol, benzylalcohol, diethyleneglycol, ethylene glycol and glycerol. Other suitable protic solvents include acids, amines, and aminoalcohols. Examples thereof include acetic acid and 2-aminoethanol. Preferably, the protic solvent is an alcohol.

The protic organic solvent and dipolar aprotic organic solvent may also be used as a mixture of different protic organic solvents and/or different dipolar aprotic solvents, provided that they are miscible.

The solvent mixture preferably has a boiling point of at least 100° C., more preferably at least 150° C., and even better at least 175° C.

Most preferably, the protic or dipolar aprotic organic solvent is DMSO, benzyl alcohol or cyclohexanol, or a mixture thereof.

The decarboxylation step in the process according to the invention takes place at elevated temperature. Practically, the solution is kept at that elevated temperature for a time sufficiently long to obtain complete decarboxylation of the ornithine.

Suitably, this elevated temperature is in the range of 140-250° C., and preferably in the range of 160-220° C., and most preferably in the range of 180-210° C. Although an elevated temperature lower than 140° C. may be applied, this is less practical since reaction times will get longer. A higher reaction temperature generally results in shorter reaction times.

An overview of solvents with different boiling temperatures and dielectric constant (relative permittivity) at 20-25° C., as reported by David R. Lide in CRC Handbook of Chemistry and Physics, CRC press, 74$^{th}$ edition, 1993-1994 and by George W Gokel in Dean's Handbook of Organic Chemistry, 2nd Edition, McGraw-Hill, 2004, is shown in Table 1.

TABLE 1

Overview of dipolar aprotic solvents with different boiling temperatures and dielectric constant at 20-25° C.

| Solvent | Formula | boiling point (° C.) | dielectric constant (at T° C.) |
|---|---|---|---|
| hexane | $C_6H_{14}$ | 69.0 | 1.890 (20) |
| pentane | $C_5H_{12}$ | 36.1 | 1.844 (20) |
| heptane | $C_7H_{16}$ | 98.0 | 1.924 (20) |
| cyclohexane | $C_6H_{12}$ | 80.7 | 2.016 (25) |
| dioxane | $C_4H_8O_2$ | 101.1 | 2.209 (25) |
| carbon tetrachloride | $CCl_4$ | 76.7 | 2.228 (25) |
| p-xylene | $C_8H_{10}$ | 138.3 | 2.270 (20) |
| benzene | $C_6H_6$ | 80.1 | 2.274 (25) |
| toluene | $C_7H_8$ | 110.6 | 2.385 (20)/2.379 (25) |
| carbon disulfide | $CS_2$ | 46.3 | 2.641 (20) |
| anisole | $C_7H_8O$ | 153.7 | 4.33 (25) |
| diethyl ether | $C_4H_{10}O$ | 34.6 | 4.335 (20) |
| chloroform | $CHCl_3$ | 61.2 | 4.806 (20) |
| N,N-dimethylaniline | $C_8H_{11}N$ | 194.2 | 4.91 (20) |
| chlorobenzene | $C_6H_5Cl$ | 132.0 | 5.71 (20)/5.621 (25) |
| ethyl acetate | $C_4H_8O_2$ | 77.0 | 6.11 (20)/6.02 (25) |
| ethyl benzoate | $C_9H_{10}O_2$ | 213.0 | 6.02 (20) |
| 1,2-dimethoxyethane (glyme) | $C_4H_{10}O_2$ | 85.0 | 7.20 (25) |
| diglyme | $C_6H_{14}O_3$ | 162.0 | 7.3 (23) |
| methyl acetate | $C_3H_6O_2$ | 56.9 | 7.03 (20)/6.68 (25) |
| tetrahydrofuran(THF) | $C_4H_8O$ | 66.0 | 7.58 (25) |
| dimethylphthalate | $C_{10}H_{10}O_4$ | 283.8 | 8.5 (24)/8.25 (25) |
| dichloromethane | $CH_2Cl_2$ | 39.8 | 9.08 (20) |
| pyridine | $C_5H_5N$ | 115.5 | 12.3 (25) |
| 2-pentanone | C5H10O | 102.3 | 15.45 (20) |
| ethyl acetoacetate | C6H10O3 | 180.4 | 15.7 (2) |
| 3-pentanone | $C_5H_{10}O$ | 101.7 | 17.00 (20) |
| cyclohexanone | $C_6H_{10}O$ | 155.6 | 18.3 (20) |
| 2-butanone | C4H8O | 79.6 | 18.51 (20) |
| acetone | C3H6O | 56.2 | 20.70 (25) |
| 2,4-pentanedione | C5H8O2 | 140.4 | 25.7 (20) |
| benzonitrile | C7H5N | 205.0 | 26.5 (20)/25.20 (25) |
| propane nitrile | C3H5N | 97.2 | 27.2 (20) |
| methylpyrrolidone | C5H9NO | 202 | 32.0 (25) |
| acetonitrile | C2H3N | 81.6 | 37.5 (20) |
| dimethylacetamide | C4H9NO | 164 | 37.8 (25) |
| dimethylformamide (DMF) | C3H7NO | 153.0 | 38.3 (20)/36.7 (25) |
| dimethylsulfoxide (DMSO) | C2H6OS | 189.0 | 48.9 (20) |

TABLE 2

Overview of protic solvents with different boiling temperatures at 0.1 MPa.

| 3-pentanol | C5H12O | 115.3 |
|---|---|---|
| 2-pentanol | C5H12O | 119.0 |
| 2-butanol | C4H10O | 99.5 |
| cyclohexanol | C6H12O | 161.1 |
| 1-octanol | C8H18O | 194.4 |
| 2-propanol | C3H8O | 82.4 |
| 1-heptanol | C7H16O | 176.4 |
| i-butanol | C4H10O | 107.9 |
| 1-hexanol | C6H14O | 158.0 |
| 1-pentanol | C5H12O | 138.0 |
| 1-butanol | C4H10O | 117.6 |
| benzyl alcohol | C7H8O | 205.4 |
| 1-propanol | C3H8O | 97.0 |
| ethanol | C2H6O | 78.5 |
| diethylene glycol | C4H10O3 | 245.0 |
| methanol | CH4O | 64.6 |
| ethylene glycol | C2H6O2 | 197.0 |

The salt solution in step (i) may be prepared by dissolving a salt of ornithine and acid in the solvent. This requires that first the salt is prepared. In a preferred embodiment of the process according to the invention, the salt solution in step (i) is prepared in situ by dissolving ornithine and an acid in the solvent.

For the acid in the salt, in principle any acid that can form a salt with ornithine may be used. Preferably, the acid used for the salt of ornithine in the process according to the invention is a strong acid chosen from the group consisting of hydrogen bromide, hydrogen chloride, hydrogen sulfate, hydrogen phosphate and hydrogen nitrate. More preferably, the acid used is hydrogen chloride and the salt is the salt of ornithine and hydrogen chloride.

The acid used in the process according to the invention may suitably be removed from the reaction mixture, formed after step (ii), by use of a stronger amine than 1,4-diaminobutane. The stronger diamine can be for example a tertiary amine. A suitable example is tri-ethylamine. The stronger amine has to be added after completion of the decarboxylation. If the tertiary amine is added to the solution prior to or during the decarboxylation step, apart from decarboxylation also ring closure reactions will occur leading to side products such as 6-aminopiperidin-2-one.

For the aldehyde or ketone, it is suitable to use an aldehyde or ketone that is inert towards DAB under the reaction conditions. Examples of a suitable aldehyde are p-methoxybenzaldehyde, propionaldehyde, benzaldehyde, o-hydroxybenzaldehyde, furfural, pyridine-2-carboxaldehyde, pyridine-3-carboxaldehyde. Examples of a suitable ketones are 2-cyclohexen-1-one, acetone, 2-butanone, 3,3-dimethyl-2-butanone, acetylacetone, 3-pentanone, acetophenone, o-hydroxyacetophenone, benzophenone, o-hydroxybenzophenone. 2,2'-dihydroxybenzophenone, benzoine, α-tetralone, and cyclohexanone.

In the process according to the invention, the aldehyde and the ketone act as a catalyst for the decarboxylation. Although these components may be present in amounts equimolar or about equimolar to the ornithine salt, or even in excess, without having a negative effect on the decarboxylation of ornithine and the formation of diamino butane, the aldehyde or ketone, or a combination thereof, needs only to be present in a catalytic amount. Suitably, the amount is in the range of 1-50 mol %, preferably in the range of 1-30 mol %, still more preferably 5-20 mol %. Herein the mol % is relative to the molar amount of the ornithine salt.

Also the concentration of the ornithine salt in the solution, and correspondingly that of the aldehyde or ketone, may be varied widely. Suitably the concentration of the ornithine salt is in the range of 2-50 wt. %, for example 5-20 wt %, and a concentration of around 10 wt % has shown to give good results. The concentration is not considered to be critical for the decarboxylation reaction, and either a lower concentration or a higher concentration may be used. Herein the weight percentage (wt. %) is relative to the total weight of the solution.

The solvent used for the process comprises a polar solvent. Herein the polar solvent is either the protic organic solvent, or the dipolar aprotic organic solvent, or the mixture thereof. Next to the polar solvent, the solvent may comprise apolar solvent, provided that the amount of polar solvent is present in a sufficient amount to induce the decarboxylation reaction of the ornithine in the ornithine salt solution.

After completion of the reaction, the diaminobutane may be isolated from the reaction mixture following routine process operations. For example, first the acid is suitably removed from the reaction mixture by use of a tertiary amine, thereby forming a salt that is filtered from the liquid components in the solution. The diaminobutane can be isolated from the other components, i.e. the solvent and the aldehyde and/or ketone, for example by distillation. Suitably, the polar solvent, i.e. the protic organic solvent, or the dipolar aprotic organic solvent, or the mixture thereof, is present in an amount of at least 50 wt. %, preferably at least 75 wt. %, relative to the total weight of the solvent. Even more preferably, the amount is at least 90 wt. %. Suitably, the amount is 100 wt. %, relative to the total weight of the solvent.

The invention is further illustrated with the following examples and comparative experiments.

EXPERIMENTS

An amount of the salt of ornithine and hydrogen chloride was weighted into a small reaction vessel equipped with a reflux cooler, an aliquot of the solvent and a small amount of aldehyde or ketone was added. The resulting solution was heated under atmospheric pressure and kept under reflux of the solvent. The conversion of the ornithine decarboxylation was followed by thin layer chromatography. The diaminobutane formation and presence or absence of side products by ring closure reaction were confirmed by thin layer chromatography and reference samples.

The solvents used in the experiments, and some properties thereof, are listed in the table 3 and 4 below. The components and the amounts thereof in the various experiments, as well as the reaction conditions and results obtained have been collected in Table 5.

TABLE 3

Protic solvents

| Abbreviation | Name | Boiling Temperature (° C.) |
|---|---|---|
| CH | cyclohexanol | 161 |
| BA | Benzylalcohol | 205 |

TABLE 4

Aprotic solvents:

| Abbreviation | Name | Relative Dielectric constant | Boiling Temperature (° C.) |
|---|---|---|---|
| DMSO | dimethylsulfoxide | 48.9 | 189 |
| DG | diglyme | 7.3 | 162 |

The results show that with the use of a solvent with sufficient polarity a good conversion is obtained, in contrast with a relatively apolar solvent like diglyme. Also the addition of triethanolamine does not help to catalyse the desired reaction.

TABLE 5

Overview of Examples and Comparative Experiments.

| Examples/ Comparative Experiments | Ornithine. HCl salt (g) | Mol (*10$^{-3}$) | Catalyst (μl) | Mol (*10$^{-3}$) | Mol % cat. | Solvent[d] | Amount (μl) | TEA[b] (μl) | T (° C.) | Hours reflux | Result[c] |
|---|---|---|---|---|---|---|---|---|---|---|---|
| | | | CHA[a] | | | | | | | | |
| E-I | 0.5 | 3 | 50 | 0.52 | 17.3 | CH | 5 | | reflux | 20 | Mix Ornithine/DAB |
| E-II | | | | | | | | | reflux | 44 | 100% DC: 100% DAB |
| E-III | 0.5 | 3 | 28 | 0.29 | 9.7 | BA | 5 | | reflux | 1.5 | 100% DC: 100% DAB |
| E-IV | 0.5 | 3 | 28 | 0.29 | 9.7 | BA | 5 | 410 | reflux | | 100% DC: DAB + RP |
| E-V | 0.25 | 1.5 | 14 | 0.146 | 9.7 | DMSO | 2.05 | | 190 | 1.5 | 100% DC |
| | | | AA[a] | | | | | | | | |
| E-VI | 0.5 | 1.5 | 28 | 0.18 | 6.1 | BA | 5 | | reflux | 24 | 100% DC |
| | | | CHA[a] | | | | | | | | |
| CE-A | 0.5 | 3 | 50 | 0.52 | 17.3 | DG | 5 | 410 | reflux | 23 | No reaction |
| CE-B | 0.5 | 3 | 50 | 0.52 | 17.3 | DG | 5 | | reflux | 20 | No reaction |
| | Ornithine | | CHA | | | | | | | | |
| CE-C | 0.5 | 3.8 | 50 | 0.52 | 13.7 | CH | 5 | | reflux | 19 | Primarily RP |
| CE-D | 0.5 | 3.8 | 50 | 0.52 | 13.7 | BA | 5 | | reflux | 19 | Primarily RP |
| CE-E | 0.39 | 3.0 | 50 | 0.52 | 17.3 | CH | 5 | | reflux | 19 | Primarily RP |
| CE-F | 0.39 | 3.0 | 50 | 0.52 | 17.3 | BA | 5 | | reflux | 19 | Primarily RP |

[a]CHA = cyclohexenon; AA = p-Anisaldehyde
[b]TEA = triethanolamine;
[c]RP = ring closed product = 6-aminopiperidin-2-one

The invention claimed is:

1. A process for preparing diaminobutane from ornithine, comprising steps of:
   (i) preparing a reaction solution comprised of:
      (a) a salt of ornithine and an acid; and
      (b) an aldehyde, a ketone or a mixture thereof; in
      (c) a solvent which comprises a dipolar aprotic organic solvent, and
   (ii) heating the reaction solution to a temperature above 100° C. thereby inducing decarboxylation of the ornithine and formation of diaminobutane.

2. The process according to claim 1, wherein the salt of ornithine is a salt of ornithine and an acid selected from the group consisting of hydrogen bromide, hydrogen chloride, hydrogen sulfate, hydrogen phosphate and hydrogen nitrate.

3. The process according to claim 2, wherein step (i) comprises dissolving ornithine and an acid in the solvent to obtain a salt solution.

4. The process according to claim 1, wherein the solvent comprises the dipolar aprotic organic solvent in an amount of at least 50 wt. %, relative to the total weight of the solvent.

5. The process according to claim 1, wherein the solvent has a boiling temperature, measured at 0.1 MPa, of at least 150° C.

6. The process according to claim 1, wherein step (ii) comprises heating the reaction solution to a temperature which is in a range of 140-250° C.

7. The process according to claim 1, wherein the dipolar aprotic organic solvent has a dielectric constant of at least 10, determined by the method according to ASTM D924, at 20° C.

8. The process according to claim 1, wherein the dipolar aprotic organic solvent is selected from the group consisting of dimethylformamide (DMF), dimethylsulfoxide (DMSO), acetonitrile, dimethyl acetamide, and mixtures thereof.

9. The process according to claim 1, wherein the solvent further comprises a protic organic solvent selected from the group consisting of alcohols.

10. The process according to claim 9, wherein the protic organic solvent is selected from the group consisting of benzyl alcohol, cyclohexanol and mixtures thereof.

11. The process according to claim 1, wherein the aldehyde is p-methoxybenzaldehyde.

12. The process according to claim 1, wherein the ketone is 2-cyclohexenone.

13. The process according to claim 1, wherein the aldehyde, ketone or mixture thereof is present in the reaction solution in an amount within a range of 0.01-0.50 mol %, relative to the molar amount of the ornithine salt.

14. The process according to claim 1, wherein the salt of ornithine and acid is present in an amount within a range of 2-50 wt. %, relative to the total weight of the reaction solution.

15. A process for preparing diaminobutane from ornithine, comprising steps of:
 (i) preparing a reaction solution comprised of:
  (a) a salt of ornithine and an acid; and
  (b) p-methoxybenzaldehyde; in
  (c) a solvent which comprises a protic organic solvent, a dipolar aprotic organic solvent or a mixture thereof, and
 (ii) heating the reaction solution to a temperature above 100° C. thereby inducing decarboxylation of the ornithine and formation of diaminobutane.

16. The process according to claim 15, wherein the salt of ornithine is a salt of ornithine and an acid selected from the group consisting of hydrogen bromide, hydrogen chloride, hydrogen sulfate, hydrogen phosphate and hydrogen nitrate.

17. The process according to claim 16, wherein step (i) comprises dissolving ornithine and an acid in the solvent to obtain a salt solution.

18. The process according to claim 15, wherein the solvent comprises the protic organic solvent, the dipolar aprotic organic solvent or the mixture thereof in an amount of at least 50 wt. %, relative to the total weight of the solvent.

19. The process according to claim 15, wherein the solvent has a boiling temperature, measured at 0.1 MPa, of at least 150° C.

20. The process according to claim 15, wherein step (ii) comprises heating the reaction solution to a temperature which is in a range of 140-250° C.

21. The process according to claim 15, wherein the dipolar aprotic organic solvent has a dielectric constant of at least 10, determined by the method according to ASTM D924, at 20° C.

22. The process according to claim 15, wherein the solvent comprises a dipolar aprotic organic solvent selected from the group consisting of dimethylformamide (DMF), dimethylsulfoxide (DMSO), acetonitrile, dimethyl acetamide, and mixtures thereof.

23. The process s according to claim 15, wherein the solvent comprises a protic organic solvent selected from the group consisting of alcohols.

24. The process according to claim 15, wherein the solvent is selected from the group consisting of dimethylsulfoxide (DMSO), benzyl alcohol, cyclohexanol and mixtures thereof.

* * * * *